United States Patent [19]

Sabia

[11] Patent Number: 4,846,194
[45] Date of Patent: Jul. 11, 1989

[54] SCOLIOSIS MEASURING APPARATUS

[76] Inventor: Michael A. Sabia, 81 Rumson Rd., Little Silver, N.J. 07739

[21] Appl. No.: 661,161

[22] Filed: Oct. 15, 1984

Related U.S. Application Data

[63] Continuation-in-part of Ser. No. 431,004, Sep. 30, 1982, abandoned.

[51] Int. Cl.[4] ............................................... A61B 5/10
[52] U.S. Cl. ....................................... 128/781; 33/512
[58] Field of Search ...................... 128/774, 781, 782; 33/174

[56] References Cited

U.S. PATENT DOCUMENTS 4,036,213 7/1977 Gregory ............................. 128/781

FOREIGN PATENT DOCUMENTS 1531671 7/1968 France ................................. 128/781
685277 9/1979 U.S.S.R. ............................. 128/781

Primary Examiner—Lee S. Cohen
Assistant Examiner—John C. Hanley
Attorney, Agent, or Firm—Charles I. Brodsky

[57] ABSTRACT

A compact, easily dismantable device adapted to rest, when in use, across the shoulders, hips and back of an individual to provide a quantitative indication of the extent of scoliosis present.

7 Claims, 2 Drawing Sheets

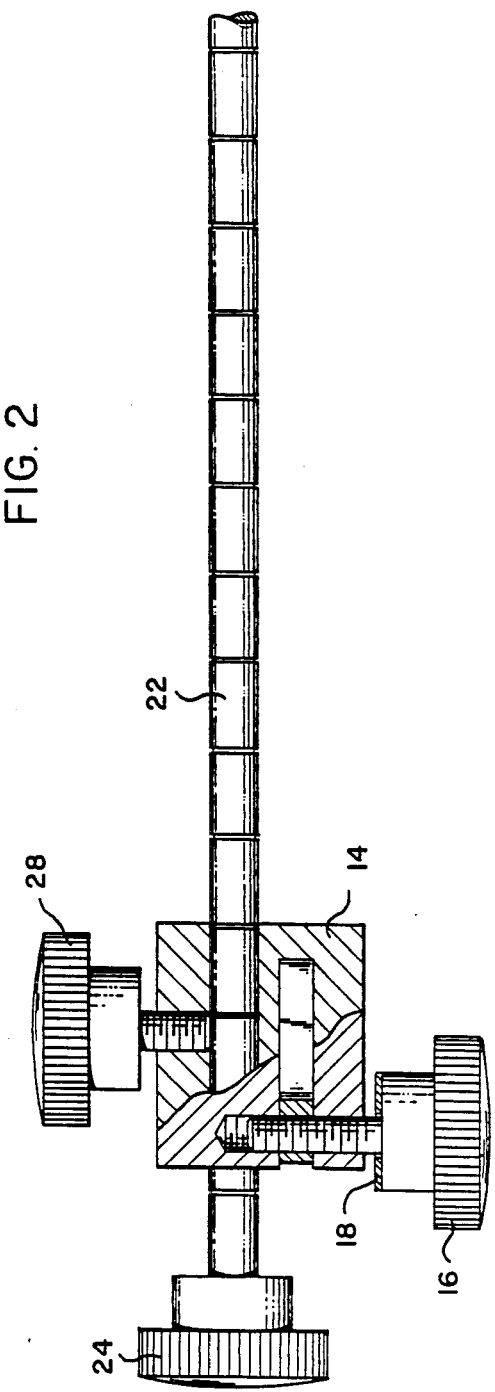
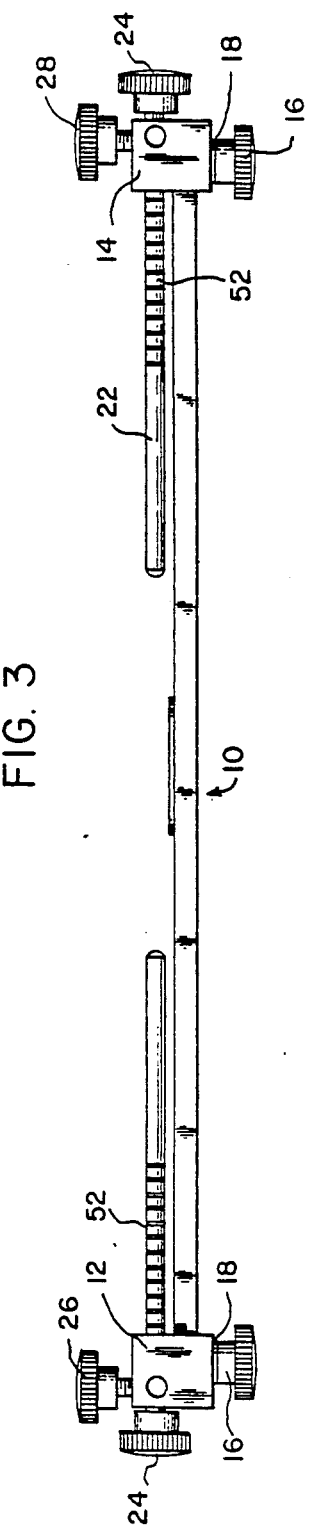

4,846,194

SCOLIOSIS MEASURING APPARATUS

This application is a continuation-in-part of my pending application, Ser. No. 06/431,004, filed Sept. 30, 1982, now abandoned.

FIELD OF THE INVENTION

This invention relates to scoliosis, a curvature to areas of the spine, in general, and to apparatus for providing a quantitative measure of the extent of any scoliosis present, in particular.

BACKGROUND OF THE INVENTION

As is well known and understood, two general methods exist by which the presence, or extent, of scoliosis in an individual can be determined. One, the least precise, is through visual observation of the alignment of a person's shoulders or hips when standing upright, and of his, or her, back when bending over. The other method commonly employs the use of x-rays, which, if measured, additionally provide information as to the extent of the scoliosis present.

As is also well known, scoliosis is often treated by casting, manipulation, exercise programs and operative techniques. Experience has shown, however, that the visual technique of observation does not adequately provide an indication as to whether progress is being made in reducing the curvature. While comparative x-rays—along with comparative measurements being made by the treating practitioner—provide accurate indications of any progress being made, such techniques are both time consuming, and costly (by virtue of the constant need for taking, developing and interpreting the x-ray), and also necessitates the availability of adequate x-ray equipment at the office location of the practitioner treating the patient.

As will thus be appreciated, a fairly simple, inexpensive, quick and easy-to-use arrangement would be desirable to provide a quantitative analysis as to whether, and to what extent, the treatment and exercises accorded are producing the desired results in reducing the incipient curvature.

SUMMARY OF THE INVENTION

As will become clear hereinafter, the apparatus of the present invention represents a compact, easily dismantable device including a transverse support member having a pair of slidably mounted rod extensions which, in one usage of the invention, are movable to rest across the shoulders and hips of a patient. An angle indicator of appropriate configuration is arranged to sit atop the transverse rod, so as to provide a needle deflection, in a preferred embodiment of the invention, indicating which shoulder or hip—and to what amount—is higher than the other, in providing a quantitative determination as to the extent of scoliosis present. First and second positive locking arrangements are included, both to securely hold the extension rod in position for use with the patient, and, also, in fixed position along the transverse rod at selected locations in accordance with the size and frame of the shoulder and hip positionings of the individual patient being tested.

In accordance with a second embodiment of the invention, the extension rods are reticuled as an aid in affording a linear measurement to be made in determining the degree of scoliosis present in an area of the back, when the patient is bent over, with the transverse rod resting on his, or her, spine—or, more generally, across the back area. Such reticulation also serves in measuring the progress of the scoliosis by releasing the rods to find the exact difference from one area of the posterior rib cage, deformable according to the severity of the rotation in the vertebral column.

In accordance with a preferred embodiment of the invention, as will be seen below, the angle indicator, the extension rods, and the slidable mounts on the transverse rod are all easily dismantable, so that the component parts making up the measuring apparatus can quickly be disassembled—both for easy storage, or portable use. To such end, an angle indicator having a magnetic base proves particularly attractive in holding to a transverse rod, or member, affording a matching magnetic capability.

BRIEF DESCRIPTION OF THE DRAWING

These and other features of the present invention will be more clearly understood from a consideration of the following description, taken in connection with the accompanying drawing, in which:

FIG. 2 is a cross-sectional view helpful in an understanding of the positive-locking aspects of the invention; and FIG. 3 shows the measuring apparatus as it might appear for easy storage and/or carrying about.

DETAILED DESCRIPTION OF THE DRAWING

Figure 1:
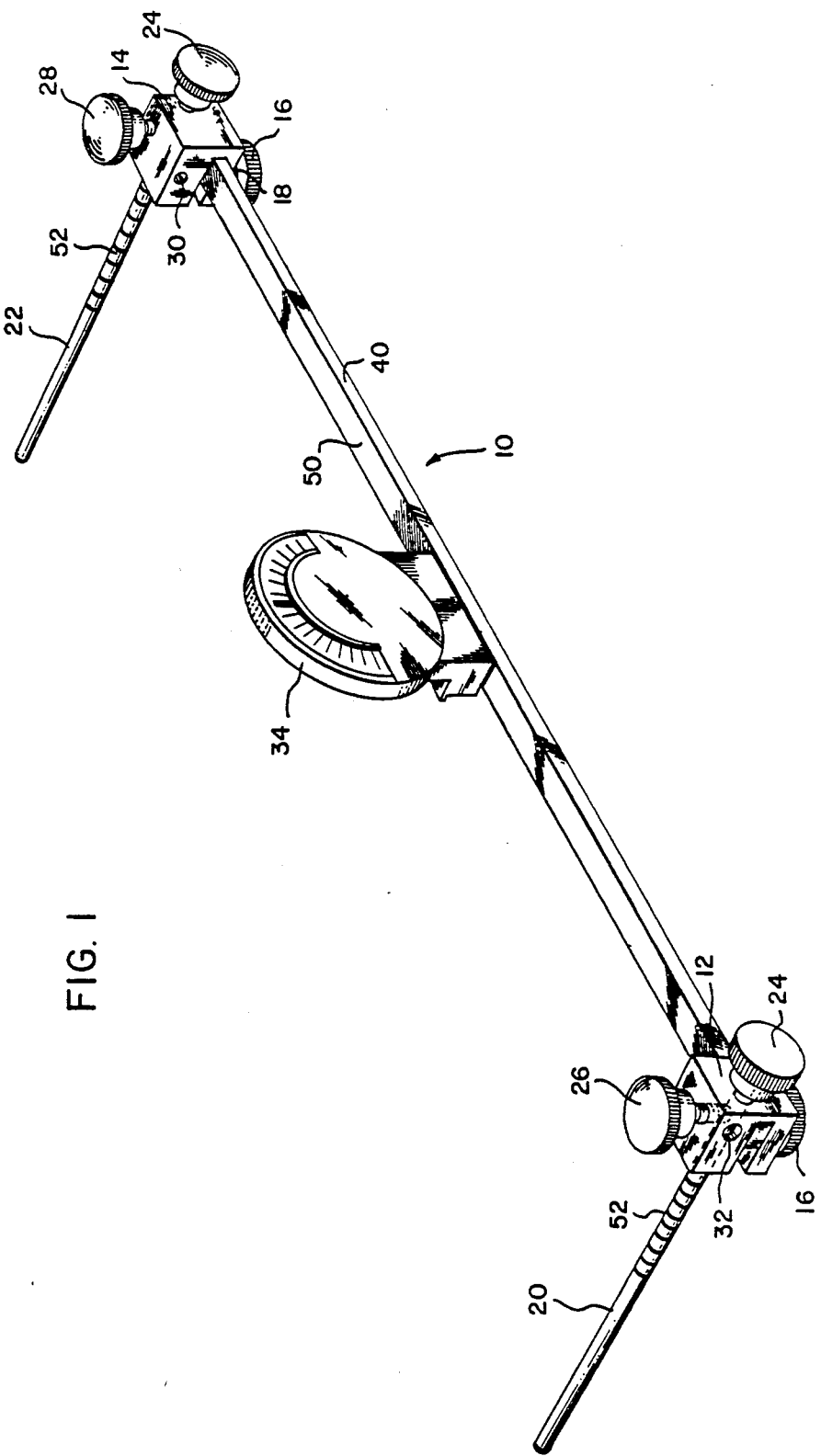
FIG. 1 is a perspective view of a preferred embodiment of a scoliosis measuring device constructed in accordance with the invention.

In the drawing, reference numeral 10 identifies the transverse support bar of the apparatus while reference numerals 12, 14 identify a pair of slidable mounts, positionably lockable in place by means of a threaded knob bolt 16 and washer 18 assembly.

A pair of extension rods 20, 22 each terminate in a knob end 24, and extend through the mounts 12, 14, to be respectively locked in place by threaded knob bolts 26, 28. A pair of apertures 30, 32 extend inwardly and through the mounts 12, 14, in co-linear alignment with the support bar 10. With the threaded knob bolts 16, 26 and 28 rotated to lock the extension rods 20, 22 in place, fixedly positioned along the transverse bar 10, the apparatus of the invention illustrated in FIG. 1 is ready for use in providing a quantitative indication of the extent of scoliosis present, once seated to rest horizontally across the shoulders and hips by means of the extension rods 20, 22 placed at such body location, in providing measurements of shoulder tilt and pelvic tilt in degrees, respectively. In measuring the shoulder tilt, it will be appreciated that the rods 20, 22 are to be placed on the acromio-clavicular articulation, whereas for measuring pelvic tilt, the rods 20, 22 are to be placed over the crest of the illium.

Measurements in the difference in the shoulder heights (i.e., shoulder tilt) will also be able to be determined when the apparatus is placed in reverse position horizontally along the back and using the extension rods 20, 22 to extend to the level of the shoulders to give a difference in millimeters, thereby affording the examiner both angular and millimeter evaluation. There, the tips of the rods 20, 22 are to be placed equal to the top of the shoulders, the rod on the higher side is released and the tip of the rod equals the shoulder height—to be read on the high side in millimeters.

More specifically, there is shown in the drawing an appropriate angle indicating device 34, preferably of a magnetic base when the transverse support is constructed of a ferrous material. While it will be appreciated that any appropriate affixation method is sufficient, a magnetic coupling permits a very easy and quick, disassembly when the apparatus is not in use. Placement of the indicator 34 anywhere along the transverse support bar 10, as in FIG. 1, then provides an angle indication as to which shoulder (or hip) is higher, if either, and with angle gradations delineated in intervals of 1°, also provides a measure of the extent of elevation, indicative of the extent of scoliosis present. Although not to be construed as being so limited, applicant has found that an "angle finder" available from Sears-Roebuck & Co. has proven useful in constructing one embodiment of the invention, although other angle indicators—as from Orthopedic Systems, 1897 National Avenue, Hayward, Calif. or from the National Scoliosis Foundation, of 48 Stone Road, Belmont, Mass. may also be used.

As will be apparent, the threaded knob bolts 16 permit the mounts 12, 14 to move in either direction, until the extension rods 20, 22 rest on the shoulders, or hips where the measurement is to be taken, depending upon the size and framing of the individual then being tested. By comparing the tilt measurements at any given time, the treating practitioner can very simply determine whether the exercise and manipulation program is being effective in achieving any of the control desired in reducing the scoliosis curvature. Instead of relying on mere visual observations to determine whether any positive effect is resulting—and instead of having to successively compare different x-ray pictures of the shoulders and hip views—, all that is necessary is for the practitioner to appropriately place the extension rods 20, 22, and read-off the indication of the angle measurer 34. By comparing the reading obtained—both in degrees and millimeters, and whether to the left, or right, an effortless comparison, quantitative in nature, can be had by checking the reading obtained with one realized previously.

In similar manner, the measuring apparatus of the drawing can be used to determine quantitatively, the scoliosis at the patient's back location, merely by rotating the FIG. 1 apparatus 90° inwardly of the plane of the drawing, (so that the transverse bar 10 would be horizontal and with the extension rods 20, 22 then pointed downwardly towards the floor area to touch the back), and by repositioning and reorienting the angle indicator 34 so that it now sits atop the bar 10 on its surface 40, instead of on the support bar surface 50, as shown in FIG. 1. For example, to measure thoracic deviation in degrees, the bar 10 is placed over the thoracic rib cage, with the patient bending forward, the mounts 12, 14 are locked in position spaced equidistant from the center of the angle indicator 34, and with the rods 20, 22 similarly locked in position, the angle deviation is read from the indicator 34, centered across the thoracic spine. To measure lumbar deviation in degrees, the same procedure is followed, except that the bar 10 and rods 20, 22 are placed over the lumbar vertebrae, centered across the lumbo-sacral spine.

To afford the examiner a second check and a second measurement, the rods 20, 22 (which are calibrated in millimeters) can again be released, and at those points of concern, the exact difference in millimeters can be read from one lumbar area to the other and from one thoracic area to the other, caused by any rotation in the vertebral column. Specifically, for measuring thoracic rib deviation, the mounts 12, 14 are locked at the crest of the rib cage, the rods 20, 22 are released, and the thoracic rib deviation measured on the high side with the indicator 34 reading 0°. For measuring lumbar deviation, the same procedure will be seen to be followed, but with the mounts 12, 14 locked at the area of the transverse process.

Again, previous angular and millimeter indications can be compared with that then obtainable, for a comparative interpretation as to the degree of success in the treatment and exercise program being administered in an attempt to reduce the extent of exhibited scoliosis.

Besides making possible quantitative measurements of shoulder tilt, thoracic deviation and lumbar deviation in degrees and in millimeters (or centimeters) and of pelvic tilt in degrees, the scoliosis measuring apparatus (i.e., Scoliometer) of the invention makes additional quantitative measurements possible, as well. Thus, with the support bar 10 arranged vertically, and with the angle indicator 34 being supported across the surface 50 instead of along that surface (as in FIG. 1) so as to face the examiner, quantitative measurements can be made of the cervical, thoracic, and lumbar anterior posterior curves. To measure the cervical curve, for example, the mount 14 is positioned so that the tip of the rod 22 will touch the spinus of cervical vertebra C4, where the rod 22 is then locked in place by the knob 28—the mount 12 is then positioned so that the tip of the rod 20 touches the spinus process of cervical vertebra C7, whereat the rod 20 is then locked in place by the knob 26—a difference in length between the extensions of rods 20-22 below 1 cm. indicates a kyphosis condition, while a difference beyond 3 cm. indicates the presence of lordosis.

In similar fashion, to measure the thoracic curve, the mount 14 is positioned such that the tip of the rod 22 touches the spinus process of cervical vertebra C7, where it is then locked in place by the knob 28. The mount 12 is then positioned to allow the tip of the rod 20 to touch the spinus process of the vertebra which is the apex of the thoracic curve, whereat the rod 20 is again locked, and by the knob 26. Any difference in rod extension readings below 1 cm. is indicative of a hypokyphotic condition, while a reading beyond 3 cm. is indicative of a more severe kyphosis condition being present.

In measuring the lumbar curve, on the other hand, the mount 14, the rod 22 and the knob 28 are all adjusted so that the tip of the rod 22 is locked in place to touch the spinus process of lumbar vertebra 15, and the mount 12, rod 20 and knob 26 arranged to lock in place the tip of the rod 20 so as to touch the most prominent tubercle at the apex of the sacrum. The lineal difference between the extension of rods 20, 22, if below a reading of 1 cm., would be indicative of a kyphotic spine, while a reading beyond 3 cm. would be indicative of an unstable lumbosacral angle.

As with the previous measurements for shoulder tilt, pelvic tilt, thoracic deviation and lumbar deviation, all readings obtained in the measurement of the cervical, thoracic and lumbar curves could be compared with those previously taken in determining the success of any exercise program prescribed—and, without the need for continually taking x-rays to quantitatively evaluate the success of any program of exercise instructions.

(In similar manners, one skilled in the art will be able to see how the bar 10, the mounts 12 and 14, the rods 20 and 22, the knobs 26 and 28, and the angle indicator 34 can be aligned for making other quantitative measurements of concern—such as of the anterior rib cage [in degrees and millimeters], of the anterior pelvic [in millimeters] and of lateral skull alignments—all through the ability to reposition, reorient, and realign the aforementioned component parts of the Scoliometer apparatus.)

As will be readily appreciated, by incorporating an angle indicator 34 of a magnetic base, it can easily be removed for storage, when the unit is to be disassembled. As will also be apparent, by unlocking the knob bolts 16, the slidable mounts 12, 14 can be removed from the support bar 10, also for storage. In like manner, by unlocking the knob bolts 26, 28, the extension rods 20, 22 can be removed—with the result being that the entire measuring apparatus can be simply taken apart and stored, when not in use. As shown in FIG. 3, an alternative arrangement can be had to completely dismantle the apparatus. There, the angle indicator 34 continues to be removed, but with the slidable mounts 12, 14 being locked in place at the end terminations of the transverse support rod 10. The knob bolts 26, 28 are then loosened to permit removal of the extension rods 20, 22, which are then re-inserted, in the direction shown, through the co-linear apertures 30, 32 to lie substantially atop the transverse support rod 10 when not in use. Once so positioned, the bolts 26, 28 can, once again, be tightened to maintain the rods 20, 22 in such alignment, and the assembly can then be stored, or even packed to fit within a brief case, or attache case, and carried about. In one embodiment of the invention, the transverse support rod 10 was fabricated of steel of dimension approximating $12'' \times \frac{1}{4}'' \times 18''$—which, with the threaded knob bolts each being of a height less than one inch, made carrying about quite simple.

As more clearly shown in the drawing of FIG. 3, the extension rods 20, 22 are reticulated in delineations of some 3/16'' each (reference numeral 52), so as to provide the indicant useful in measuring the thoracic and lumbar curvatures and the conditions of the cervical, thoracic and lumbar spinal curves. More specifically, once it is seen that an angle indication is produced by deflection in the unit 34 for the thoracic and lumbar deviation measurements, it becomes but a simple matter to raise the one extension rod 20, or 22, in a direction to bring the needle deflection back to zero in the indicator. With the reticulations on the rod, a linear measurement can be noted, and determined, as another quantitative indicant of the extent of scoliosis present at that time. Subsequent comparisons made at a later date, after treatment, exercise programs, etc. have transpired, is then effective as showing a measure of success through the treatment accorded.

While there have been described what are considered to be preferred embodiments of the present invention it will be readily appreciated by those skilled in the art that modifications can be made without departing from the scope of the teachings herein. Thus, while the Scoliometer of the invention has been described as including an angle indicator, for example, of a magnetic base material, it will be appreciated that such is for the purpose of easy break-down of the measuring apparatus and, in general, any appropriate means of affixation—of the other alternative devices described or of others equally useful as well—would be similarly beneficial. For at least such reason, therefore, resort should be had to the claims appended hereto for a true understanding of the scope of the invention.

I claim:

1. Apparatus for measuring the extent of scoliosis in an individual, comprising:
    a transverse support member;
    first and second mounting means predeterminedly positioned along said support member;
    means for locking said mounting means in place at any selected position along said support member;
    a pair of reticuled members adopted for respective extension through individual ones of said mounting means to rest at the body location of said individual to be measured;
    with said reticuled members extending in a direction substantially perpendicular to the longitudinal direction of said transverse support member;
    means adapted to releasably lock the extension of said reticuled members through said mounting means;
    and means locatable on said support member for providing an angle indication as to any existing elevational difference between said reticuled members when rested at said body locations;
    with said angle indicating providing means being adjustable in orientation with respect to the position of said support member when in use;
    whereby, with said reticuled member extension locking means adapted to release one of said pair of reticuled members through said mounting means, lineal measurement of any existent scoliosis is obtainable;
    and whereby, with said reticuled member extension locking means adapted to lock both of said pair of reticuled members through said mounting means, angulation measurement of any existent scoliosis is independently obtainable.

2. The apparatus of claim 1 wherein said angle indication providing means is adapted for removal from said support member when said apparatus is not in use.

3. The apparatus of claim 1 wherein said angle indication providing means is locatable on said support member in magnetically attracting relationship.

4. The apparatus of claim 1 wherein said mounting means locking means is adjustable for holding said mounting means in place along said support member when said apparatus is in use and for permitting removal of said mounting means from said support member when said apparatus is not in use.

5. The apparatus of claim 1 wherein said reticuled member extension locking means is adjustable for holding said reticuled members in cooperating relationship with said mounting means when said apparatus is in use and for permitting removal of said reticuled members from said mounting means when said apparatus is not in use.

6. The apparatus of claim 1 wherein said mounting means are apertured to align said reticuled members in a plane co-linear with the longitudinal dimension of said transverse support member when said apparatus is not in use.

7. The apparatus of claim 1 wherein said reticuled members are reticulated along their length in predetermined amounts, for providing a linear indication as to existing elevational differences between said reticuled members when rested at selected body locations of said individual.

* * * * *